(12) United States Patent
Brown et al.

(10) Patent No.: US 7,672,428 B1
(45) Date of Patent: Mar. 2, 2010

(54) RADIOTHERAPY APPARATUS

(75) Inventors: Kevin John Brown, West Sussex (GB); Paul Boxall, West Sussex (GB)

(73) Assignee: Elekta AB (PUBL), Stockholm (SE)

( * ) Notice: Subject to any disclaimer, the term of this patent is extended or adjusted under 35 U.S.C. 154(b) by 0 days.

(21) Appl. No.: 11/435,927

(22) Filed: May 17, 2006

(51) Int. Cl.
*H05G 1/44* (2006.01)
*H05G 1/20* (2006.01)
*A61N 5/10* (2006.01)

(52) U.S. Cl. .......................... 378/65; 378/97; 378/106; 378/108

(58) Field of Classification Search .................. 378/62, 378/65, 97, 98.7, 105–108, 114, 115, 117; 600/427
See application file for complete search history.

(56) References Cited

U.S. PATENT DOCUMENTS

| | | | | |
|---|---|---|---|---|
| 4,532,644 A | * | 7/1985 | Yamaguchi et al. | 378/16 |
| 4,595,949 A | * | 6/1986 | Fenster et al. | 378/98.7 |
| 4,803,716 A | * | 2/1989 | Ammann et al. | 378/155 |
| 5,668,847 A | * | 9/1997 | Hernandez | 378/65 |
| 6,069,938 A | * | 5/2000 | Chornenky et al. | 378/122 |
| 6,385,280 B1 | * | 5/2002 | Bittl et al. | 378/16 |
| 7,016,468 B1 | * | 3/2006 | Krema et al. | 378/112 |
| 7,372,944 B2 | * | 5/2008 | Bernhardt et al. | 378/106 |
| 2003/0072411 A1 | * | 4/2003 | Welsh | 378/65 |

* cited by examiner

*Primary Examiner*—Edward J Glick
*Assistant Examiner*—Thomas R Artman
(74) *Attorney, Agent, or Firm*—Z. Peter Sawicki; Westman, Champlin & Kelly, P.A.

(57) ABSTRACT

Recent advances in treatment planning and in the apparatus able to deliver such plans has called for the dose rate, i.e. the instantaneous power output of the radiation source, to be varied with time. This presents a difficulty in that the checking systems must monitor a varying power level against a varying valid range. We therefore monitor, instead, the energy of the individual pulses that form the beam. Known checking systems average out many pulses to determine the recent average power output by checking an ionization chamber every 100 ms or so. By reducing that time to less than a few milliseconds, a single pulse can be captured. The usual manner of varying the output of a radiation source of this type is to vary the pulse repetition frequency (PRF) and therefore the measured power output will remain constant notwithstanding changes to the time-averaged power output, and can be compared to a standard.

7 Claims, 2 Drawing Sheets

RADIOTHERAPY APPARATUS

FIELD OF THE INVENTION

The present invention relates to improvements in or relating to radiotherapy apparatus.

BACKGROUND OF THE INVENTION

Radiotherapy apparatus employ a source of ionizing radiation that is directed towards a cancerous region of a patient. Harm is caused to the cancerous tissue, thereby moving the patient towards cure.

The radiation is equally apt to cause harm to healthy tissue, and therefore a number of steps are taken to limit the exposure of non-cancerous tissue to radiation, and to enhance the exposure of cancerous tissue. Collimators and treatment plans seek to direct the radiation to the target areas, to limit exposure in other areas, and (where necessary) to balance these two objectives satisfactorily.

As the systems become more complex, the opportunity for error as a result of system malfunction becomes in principle greater, and therefore additional layers of checking and control circuitry are added to make this in fact unlikely. These additional layers are themselves theoretically at risk of malfunction and therefore the system is designed to fail safe, i.e. to cease the treatment if anomalies are detected.

One such check is directed at the recent average power output of the radiation source. If this power output were to deviate exceptionally from the expected level, then this is generally regarded as an indication that some otherwise undetected malfunction has occurred with the radiation source and that might cause the distribution of the dose to the tumor and/or the healthy tissue to be different from the planned distribution. Accordingly, the recent average power output of the source is checked and the treatment stopped if this falls outside acceptable limits.

SUMMARY OF THE INVENTION

Recent advances in treatment planning and in the apparatus able to deliver such plans has called for the dose rate, i.e. the instantaneous power output of the radiation source, to be varied with time. An example is our co-pending International application filed at the EPO Receiving Office on 27 Apr. 2006 and entitled "Radiotherapeutic Apparatus", the disclosure of which is hereby incorporated by reference. This presents a difficulty in that the checking systems must monitor a varying power level against a varying valid range.

We therefore propose to monitor, instead, the energy of the individual pulses that form the beam. A therapeutic accelerator does not generally run at full power continually, but generally produces a series of pulses approximately a few microseconds long, every few milliseconds. Known checking systems average out many pulses to determine the recent average power output by checking an ionization chamber every 100 ms or so. By reducing that time to less than a few milliseconds, a single pulse can be captured. The usual manner of varying the output of a radiation source of this type is to vary the pulse repetition frequency (PRF) and therefore the measured power output will remain constant notwithstanding changes to the time-averaged power output, and can be compared to a standard.

Thus, in one aspect the present invention relates to a radiotherapeutic apparatus comprising a source of ionizing radiation, a detector arranged to measure the output power of the source, and a control apparatus arranged to monitor the detected output and control the apparatus in dependence thereon, wherein the source emits radiation in a pulsed manner and the detector is arranged to measure the output power of each pulse.

Many detectors for radiotherapeutic use, such as ionization chambers and associated charge measurement devices, are arranged to measure the energy output since the last measurement. In that case, it is convenient to trigger a measurement event of the detector between each pulse.

In essence, the sampling rate for the detector should be of the same order of magnitude as the pulse rate of the source. Thus, in another aspect, the present invention provides a radiotherapeutic apparatus comprising a source of ionizing radiation, a detector arranged to receive sequential triggers and measure the energy output of the source between triggers, and a control apparatus arranged to monitor the detected output and control the apparatus in dependence thereon, wherein the source emits radiation in a pulsed manner and the trigger rate of the detector is of the same order of magnitude as the pulse rate of the source.

This approach to measurement is inspired by the need to monitor a radiotherapeutic apparatus in which the output of the source is variable by varying the pulse repetition frequency. However, there is no reason in principle why it should not be applied to other apparatus.

BRIEF DESCRIPTION OF THE DRAWINGS

An embodiment of the present invention will now be described by way of example, with reference to the accompanying figures in which.

DETAILED DESCRIPTION OF ILLUSTRATIVE EMBODIMENTS

Figure 1:
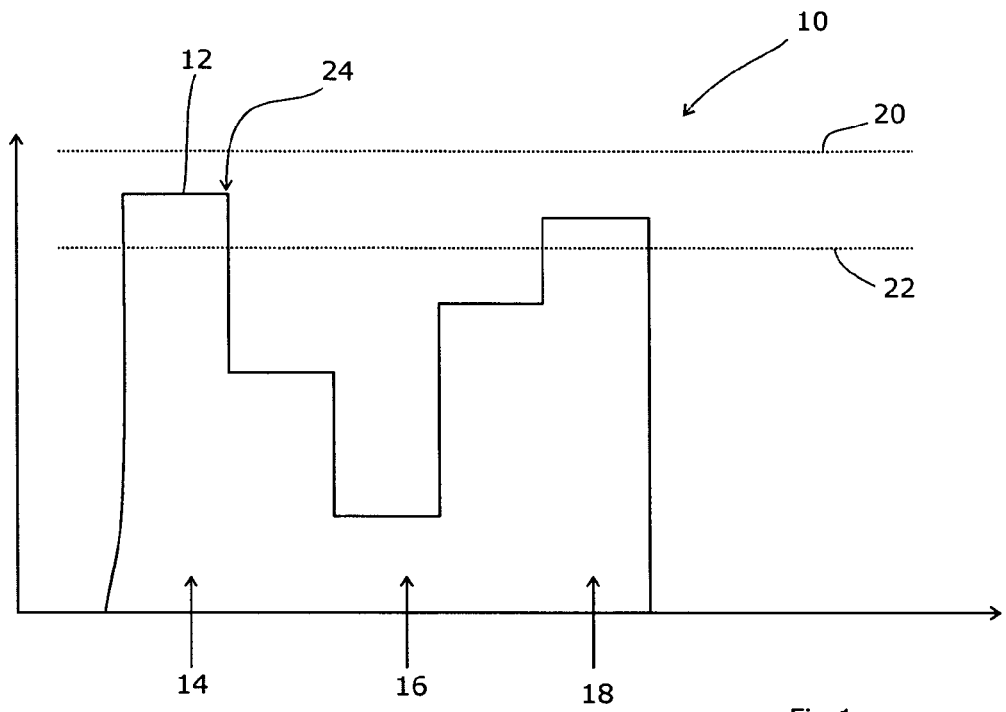
FIG. 1 shows a plot of output power with time.

Referring to FIG. 1, a plot 10 of required power output 12 against time is shown. This might be required for (by way of example) an advanced MAT treatment plan in which the radiation source is being rotated about the patient in order to treat a tumor near to sensitive structures, such as a prostate tumor which is close to the bladder and rectum. As the source rotates around the patient, there is initially a clear view of the tumor and the dose rate is high as in region 14. As rotation continues, a sensitive area begins to obscure the tumor and the dose rate is reduced as in region 16. Further rotation brings the sensitive region out of line with the tumor and the dose rate can be increased again as shown in region 18.

Dotted lines 20, 22 show the upper and lower limits for the permitted output power. If the output power exceeds the upper limit or falls below the lower limit, monitoring circuitry prompts the apparatus to cease the treatment for the reasons given above. FIG. 1 shows a relatively wide band for reasons of clarity.

The actual power level is, in practice, monitored by detecting the effect of the output radiation on an ionization chamber placed in the path of the radiation beam. The charge from the ionization of a suitable gas contained in the chamber as a result of the radiation passing through it is accumulated in a charge measurement system. The amount of accumulated charge can be measured (periodically) and then discharged. The amount of accumulated charge is an indication of the total radiation that has passed through the chamber since the last discharge. Such chambers are well known and well characterized.

Whilst this simple form of monitoring is suited to devices running at a constant power level, FIG. 1 shows that when the power level is first reduced at point 24, the low power warning will be triggered and the treatment ended. Clearly, this is a false alarm.

Figure 2:
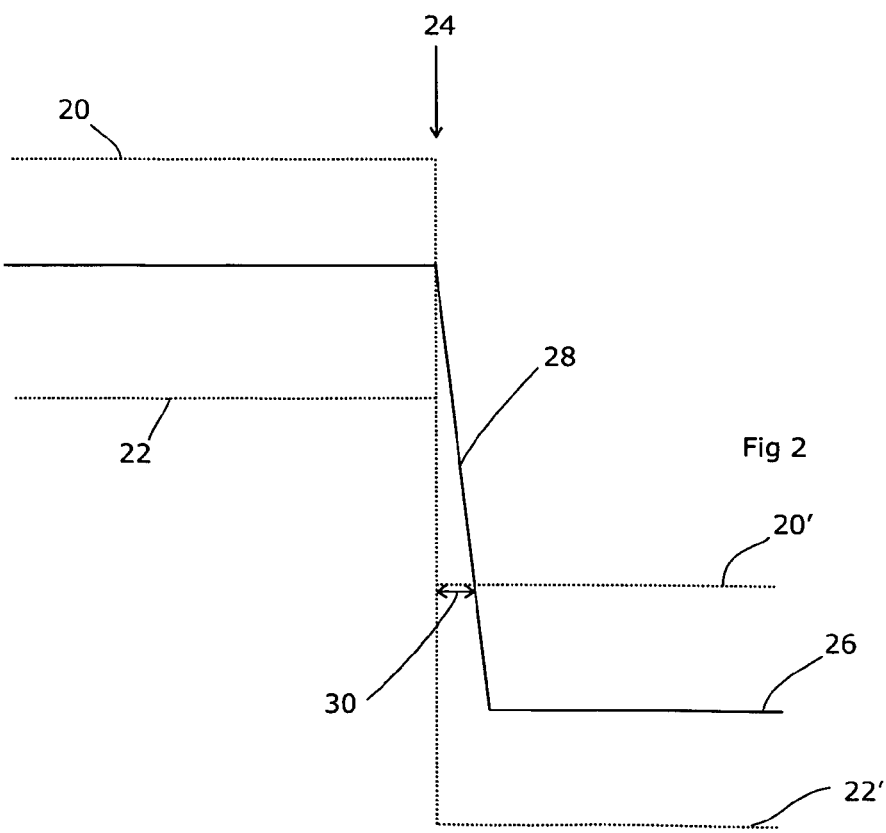
FIG. 2 shows part of the plot of FIG. 1 in more detail.

It might be proposed to change the trigger thresholds as the power is changed. FIG. 2 shows why this measure will not be reliable. Given that the thresholds are being monitored in software, this change would happen almost instantaneously. FIG. 2 shows that at time point 24, the upper and lower thresholds 20, 22 are each reduced to new levels 20', 22' that bound the new power level 26. This might be expected to have the desired result.

However, there are many reasons why the change in power from the radiation source and the change in the trigger threshold might not occur synchronously. For example, communication delays between the computer and the linear accelerator control system. In addition, the power is actually delivered as a series of pulses, typically of 2-3 µs at 400 Hz i.e. every 2.5 ms, a duty cycle of 1 in 1000. The power level is typically measured every 100 ms, during which time approximately 40 pulses will have happened. The accumulated charge from the ionization chamber will therefore reflect an integral over those 40 pulses. The power level is changed by adjusting the frequency of the pulses, and thus the first integral after a change will reflect some pulses at the higher rate and some at the lower rate. Accordingly, unless the change in power level happened to be synchronized to the power level detection, the subsequent detected power level will be midway between the old and new power levels. This lag must be added to the response time of the accelerator.

FIG. 2 therefore shows a slope 28 in the measured power level 12. A period 30 therefore exists during which the measured power level lies outside the allowed limits 20', 22'. This will prompt the apparatus to cease the treatment, unnecessarily.

Figure 3:
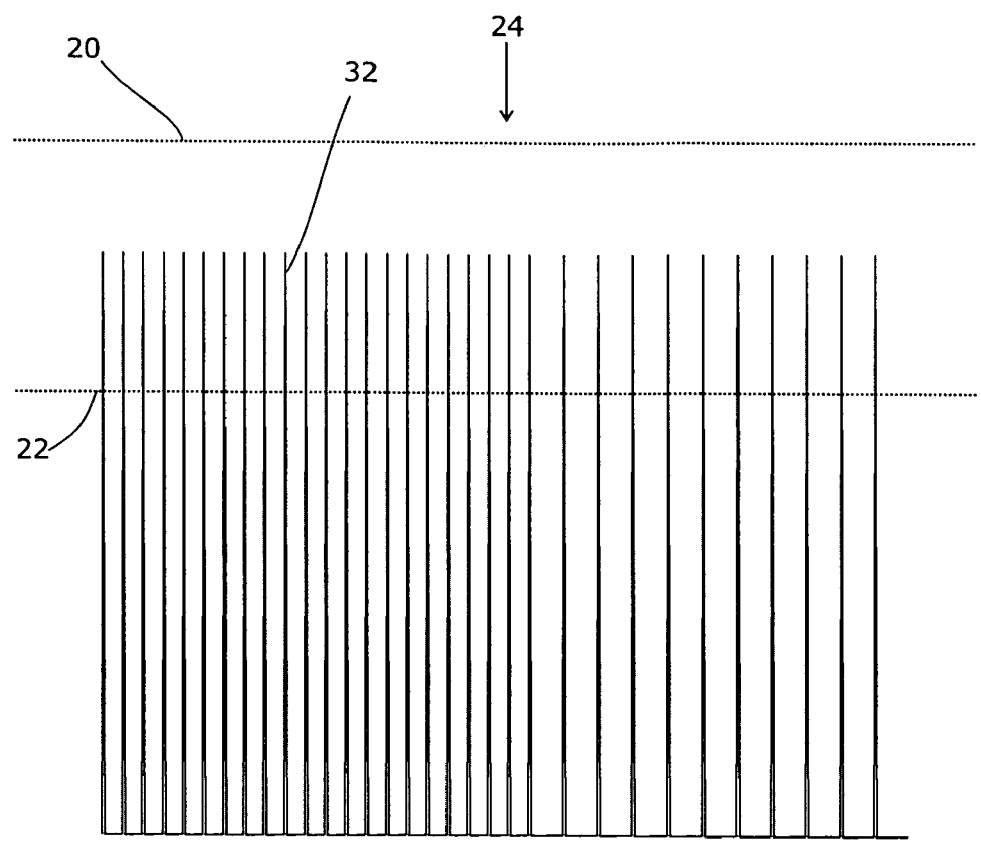
FIG. 3 shows the variation output power with time in greater resolution.

FIG. 3 shows the effect of monitoring the power level of individual pulses. This can be achieved by detecting the accumulated charge from the ionization chamber after every pulse, such as by way of a 1 ms measurement, triggered to synchronize with the pulse. Each pulse 32 is of the same height even after time point 24 when the pulse repetition frequency (PRF) is reduced so as to reduce the effective power level. This means that the pulse heights remain within the acceptable limits 20, 22 at all times, provided the apparatus is operating correctly.

Figure 4:
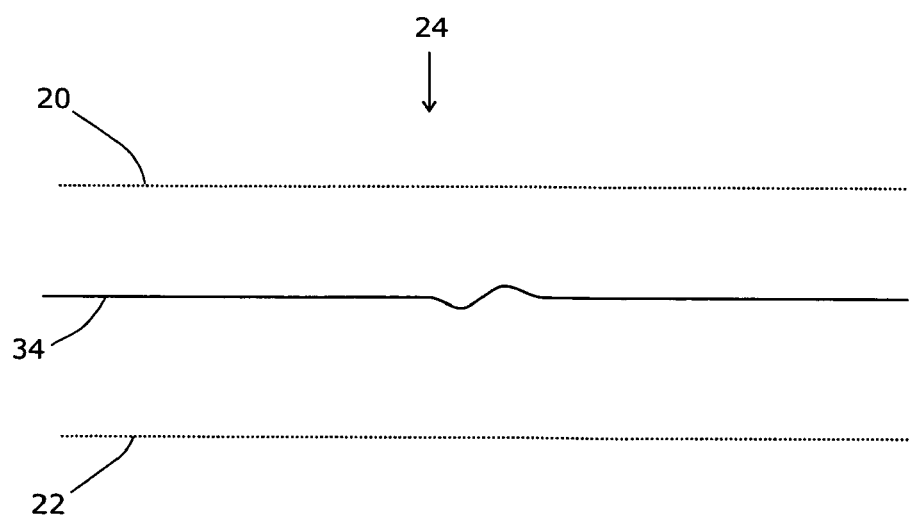
FIG. 4 shows the output monitored according to the present invention.

A change in the PRF may have some effect on the operating parameters of the accelerator that temporarily affect the pulse height. However, these effects are likely to be small in comparison with the pulse height and will not affect the correct delivery of the radiation distribution. FIG. 4 shows such a trace of pulse height with time. The small nature of such perturbations will not exceed properly set thresholds 20, 22.

It will of course be understood that many variations may be made to the above-described embodiment without departing from the scope of the present invention.

Although the present invention has been described with reference to preferred embodiments, workers skilled in the art will recognize that changes may be made in form and detail without departing from the spirit and scope of the invention.

What is claimed is:

1. A radiotherapeutic apparatus comprising a source of ionizing radiation, a detector arranged to measure an output energy of the source, and a control apparatus arranged to monitor the measured output energy during treatment of a patient, wherein the source emits a therapeutic beam of radiation in a pulsed manner as a series of pulses, the detector is synchronized with the source to measure an output energy of each pulse of the series of pulses, and the control apparatus is arranged to control pulse energy of a subsequent pulse of the series of pulses in dependence on the measured output energy of each pulse during treatment of the patient.

2. The radiotherapeutic apparatus according to claim 1, wherein the detector is arranged to measure the energy output since the last measurement.

3. The radiotherapeutic apparatus according to claim 1, wherein the detector is a ionization chamber.

4. The radiotherapeutic apparatus according to claim 1, wherein a measurement event of the detector is triggered between each pulse.

5. The radiotherapeutic apparatus according to claim 1, wherein the therapeutic beam of radiation is variable by varying a pulse repetition frequency.

6. A radiotherapeutic apparatus comprising a source of ionizing radiation, a detector arranged to receive sequential triggers and measure energy output of the source between triggers, and a control apparatus arranged to monitor the measured energy output of individual pulses of radiation emitted by the source and to provide an indication in response to the measured energy output deviating from a defined range during treatment of a patient, wherein the source emits a therapeutic amount of radiation in a pulsed manner as a series of pulses, the sequential triggers occur between pulses of radiation emitted by the source such that the detector measures the energy output of each pulse of the series of pulses, and a trigger rate of the detector is of the same order of magnitude as a pulse rate of the source.

7. The radiotherapeutic apparatus of claim 6, wherein the control apparatus is configured to control the source to cease emitting radiation in the pulsed manner when the measured energy output deviates from the defined range.

\* \* \* \* \*